US005958379A

United States Patent [19]

[11] Patent Number: 5,958,379
[45] Date of Patent: Sep. 28, 1999

Regenold et al.

[54] PHARMACEUTICAL COMPOSITION

[75] Inventors: Juergen Regenold, Ebringen; Carl Artmann, Gauting; Joachim Roeding, Badenweiler, all of Germany

[73] Assignee: Mika Pharma Gesellschaft Fuer Die Entwicklung Und Vermarktung Pharmazeutischer Producte MBH, Limburgerhof, Germany

[21] Appl. No.: 08/809,384

[22] PCT Filed: Sep. 28, 1995

[86] PCT No.: PCT/DE95/01351

§ 371 Date: May 27, 1997

§ 102(e) Date: May 27, 1997

[87] PCT Pub. No.: WO96/10389

PCT Pub. Date: Apr. 11, 1996

[30] Foreign Application Priority Data

| | | | |
|---|---|---|---|
| Sep. 30, 1994 | [DE] | Germany | 44 34 995 |
| Sep. 30, 1994 | [DE] | Germany | 44 35 010 |

[51] Int. Cl.$^6$ ..... A61K 9/00; A61K 38/00; A61K 31/56; A61K 31/24

[52] U.S. Cl. ..... 424/47; 514/2; 514/179; 514/535; 514/573; 514/951

[58] Field of Search ..... 514/573, 951, 514/2, 535, 179; 424/47

[56] References Cited

U.S. PATENT DOCUMENTS

| | | | |
|---|---|---|---|
| 3,592,891 | 7/1971 | Dawson et al. | 514/305 |
| 4,144,319 | 3/1979 | Willer et al. | 424/45 |
| 4,464,378 | 8/1984 | Hussain | 514/282 |
| 5,008,293 | 4/1991 | Berger | 514/718 |
| 5,192,528 | 3/1993 | Radhakrishnan et al. | 424/45 |
| 5,431,914 | 7/1995 | Adekunle et al. | 424/401 |

FOREIGN PATENT DOCUMENTS

| | | |
|---|---|---|
| 0 103 783 A2 | 3/1984 | European Pat. Off. . |
| 0 130 550 A2 | 6/1984 | European Pat. Off. . |
| 0 253 619 A2 | 1/1988 | European Pat. Off. . |
| 0 267 050 A2 | 5/1988 | European Pat. Off. . |
| 0 292 100 A1 | 11/1988 | European Pat. Off. . |
| 0 391 342 A1 | 10/1990 | European Pat. Off. . |
| 0 439 042 A1 | 7/1991 | European Pat. Off. . |
| 41 21 389 A1 | 6/1991 | Germany . |
| 41 22 661 A1 | 2/1992 | Germany . |
| 42 16 644 A1 | 12/1992 | Germany . |
| WO 87/07504 | 12/1987 | WIPO . |
| WO 88/04556 | 6/1988 | WIPO . |
| WO 91/07947 | 6/1991 | WIPO . |
| WO 94/05330 | 3/1994 | WIPO . |

*Primary Examiner*—Kevin E. Weddington
*Attorney, Agent, or Firm*—Proskauer Rose LLP

[57] ABSTRACT

A pharmaceutical composition containing at least one systemically and/or locally effective, topically applicable active substance, preferably selected from the group consisting of local anaesthetics, anti-allergic agents, dermatics, active substances for influenzal infections and colds, active substance for the treatment of neuropathies, chemotherapeutics, quinine, thalidomide, analgesics, non-steroid antirheumatics, opiate receptor agonists, opiate receptor antagonists, substances inhibiting the blood coagulation, substances inhibiting platelet aggregation, corticoids, histamine antagonists, anti-diabetics, regulatory peptides and the inhibitors thereof, prostaglandins and/or the esters thereof and/or antivirally effective substances is described. The pharmaceutical composition has such a liquid consistency that it is sprayable in droplets, and that after being sprayed the composition forms a preparation within short time, preferably within a time of less than 4 seconds, on the sprayed body surface, particularly on the sprayed skin or mucous membrane, whereby, compared to the original liquid composition, this preparation is formed in such a preparation which has an essentially higher concentration of the active substance and which contains the active substance in a finely divided way.

54 Claims, No Drawings

PHARMACEUTICAL COMPOSITION

The present invention is directed to a pharmaceutical composition with the characteristics of the generic part of patent claim 1.

Pharmaceutical compositions with the active substance mentioned in the main claim are usually formed as injectable composition or as tablets, dragees or suppositories, in order to guarantee that way that the respective active substance is transported to the site of action within a very short time by means of the corresponding body liquid, particularly by means of the blood, in order to systemically cause the desired effect.

Only in a few exceptional cases the active substances mentioned in the main claim are formed in the way that they can be topically applied, whereby such an application is suitable preferably for a local application, meaning for the locally limited external treatment. Rheumatic ointments with non-steroid anti-rheumatics or heparin-containing ointments or creams are for example known which, however, are locally applied to the infected body zones where they effect in a regionally limited way.

Herefore it is necessary to apply these ointments or creams to the regionally limited, infected or suffering body zone and to rub them in, which is often experienced as being painful when locally limited infections or injuries being sensitive to pressure are treated.

The initially mentioned systemically effective tablets, dragees, suppositories, injections or infusions cause essential problem when the patients have to be treated over a longer time period. Such problems, which do not depend on the active substance itself but on the afore described known applications, express themselves, for example, in stomachache, irritations of the anus and/or the intestines, or bruises from infusions or injections, or obliteration of veins, which sometimes leads to the fact that the form of application has to be changed or that the application of the respective active substance has even to be renounced on.

The present invention has the object of providing a pharmaceutical composition of the indicated sort, whereby this pharmaceutical composition is locally as well as systemically applicable in a particularly simple manner and highly effective.

This object is realised according to the invention by a pharmaceutical composition with the characteristics of the patent claim 1.

The inventive pharmaceutical composition with at least one systemically and/or locally effective, topically applicable active substance, being preferably selected from the group consisting of local anaesthetics, anti-allergic agents, dermatics, active substances for influenzal infections and colds, active substances for the treatment of neuropathies, chemotherapeutics, quinine, thalidomide, analgesics, non-steroid antirheumatics, opiate receptor agonists, opiate receptor antagonists, substances inhibiting the blood coagulation, substances inhibiting platelet aggregation, corticoids, histamine antagonists, anti-diabetics, regulatory peptides and the inhibitors thereof, prostaglandins and/or the esters thereof and/or antivirally effective substances, is not provided as tablet, dragee, suppository, injection or infusion, cream or ointment, as the initially mentioned prior art claims, instead it has such a liquid consistency that it can be sprayed in droplets, whereby after being sprayed the composition forms a preparation within short time, preferably within a time of less than 4 seconds, on the sprayed body surface, particularly on the sprayed skin or mucous membrane, whereby, compared to the original liquid composition, this preparation is formed in such a preparation which has an essentially higher concentration of the active substance and which contains the active substance in a finely divided way.

In order to avoid confusions and for the easy understanding, the form of application which can be sprayed in droplets, meaning thus the form of application being available in the trade, is designated in the present application as inventive pharmaceutical composition, whereas the form of application which is formed from the sprayed inventive composition by evaporation or vaporization of the liquid of the liquid composition on the sprayed body surface, particularly on the sprayed skin and/or mucous membrane, is continuously designated with the term preparation.

The inventive composition shows a range of advantageous. First of all it is to be noted that, caused by its liquid formulation, the inventive composition can be applied in an essentially easier and more exact way than the unctuous or creamy known products even to body zones at which the known creams and ointments can not be applied, as for example at the temple zone, since for the application of the liquid inventive composition it is only necessary to spray a given volume, whereas the application of the unctuous, respectively creamy, known products requires an easily accessible and non-hairy skin section and visual estimation of the cream amount or the ointment amount. When the inventive liquid composition is used, smearing and soiling of the cloths can easily avoided since a directed spraying also of badly accessible body zones is essentially easier than the spreading and rubbing of the known ointments or creams on large surfaces. According to the inventive composition exactly this spreading and rubbing is not necessarily required, contrarily to the known products, since the preparation formed on the body surface by evaporation or vaporization of the liquid already has an ideal fine division of the active substances, so that according to the topical systemic and/or local application of the inventive composition a pressure pain does correspondingly not occur. Furthermore, many patients experience the cooling caused by the evaporation or the vaporization of the liquid out of the inventive composition as particularly pleasant and pain-relieving, whereby the patient has the impression that the inventive composition initiates a spontaneous healing already after the first topical application.

In addition to that further advantages are connected with the topical local and/or systemic application of the inventive composition. Depending on the fact that during or after the application of the liquid inventive composition a preparation is formed by the evaporation or the vaporization of the liquid, the preparation having an essentially higher concentration of the at least one active substance than the originally used liquid composition, it can be renounced, during the manufacturing of the inventive liquid composition, on solving, dispersing or emulsifying a particularly high concentration of the at least one active substance in the inventive liquid composition with an correspondingly high expense and/or by adding unnecessary additives, if this is desired or required, whereby the manufacturing of the inventive liquid composition is simplified. This is particularly important for such active substances that can be emulsified, respectively dispersed, in the respective liquid only by adding an emulsifying agent, respectively a dispersing agent, as this is examplarily the case for certain active substance being injectable or applicable by means of an infusion or for active substance basing on heparin. Moreover, the at least one active substance of the inventive liquid composition exists in the preparation formed on the respective body surface in an ideal fine division after the droplet-like spraying, so that this finely divided active substance has an extremely small particle size, which again facilitates the transport of the active substance, for example, through skin barriers or tissue cell walls, and that thus the active substance enters the corresponding body liquid, preferably the blood, whereby then the active substance is transported to the site of action and thus effectuates such a systemic healing. Caused by this fine division of the active substance, the inventive composition is highly effective when used for local application, so that it is comprehensible that the inventive composition being applied for a local therapy causes a much faster healing than the usual and known locally applicable ointments and creams.

A further advantage of the inventive composition is that in the simplest case, after the evaporation or the vaporization of the liquid, the at least one active substance is provided in the thus formed preparation as single substance and without any auxiliary substances on the respective body surface, particularly on the sprayed skin or the mucous membrane, so that then this at least one active substance necessarily diffuses or migrates into the body without being negatively influenced by such auxiliary substances existing in the known ointments or creams, whereby all this is not the case for the known cream-like or ointment-like compositions.

Hereby it is often observed that, for example, the major substance of the ointment or the major substance of the cream avoids or impedes the migration, respectively the diffusion, of the active substance into the body by interacting with the active substance, so that hereby the healing is retarded or essentially prolonged, which does not occur in the inventive composition. This is a reason why the known cream-like or ointment-like compositions, compared to the inventive composition, can be only applied with a low success for the treatment of locally limited infections of the skin.

In comparison with the initially mentioned systemically effective forms of application (e.g. tablet, dragee, suppository, injection, infusion) the inventive composition has the crucial advantage of being applicable over a longer time period without showing all the afore mentioned side effects and problems since the inventive composition does not introduce the active substance into the body by means of the gastrointestinal tract or by means of a direct injection into the blood circulation, but by applying it to a corresponding skin or mucous membrane, so that subsequently to the transport of the active substance through the skin, respectively the mucous membrane, this active substance is transported by means of the body liquid, particularly the blood, to the site of action where it causes the desired systemic effect.

A first embodiment of the inventive pharmaceutical composition provides that hereby the composition forms the preparation on the sprayed body surface within a time of less than 2 seconds, preferably within a time of between 1 second and 0.01 seconds. During the topical application or immediately hereafter the evaporation or the vaporization of the liquid inventive composition takes places within the afore mentioned times, so that, caused by the afore indicated relatively short times, it is avoided that, even in the case of an undesired overdosing or of an application at highly vaulted or inclined body surfaces, a part of the inventive liquid composition flows off the correspondingly sprayed body surface or flows in an undesired way.

In order to obtain in the inventive composition a particularly fast evaporation, respectively vaporization, of the liquid of the liquid composition, whereby the particle size of the at least one active substance as well as its fine division in the preparation forming on the topically treated skin surface is determined, the inventive composition preferably comprises additionally to the at least one active substance such liquids which allow a spraying of the inventive composition in droplets with a droplet diameter of between 1 $\mu$m and 1,000 $\mu$m, preferably in droplets with a droplet diameter of between 10 $\mu$m and 100 $\mu$m. In order to obtain this advantageous droplet diameters during the spraying of the inventive composition, particularly the surface tension of the liquid inventive composition, the zeta potential thereof, the kind of the liquid, the chemical construction of the inventive liquid composition and/or the viscosity of the inventive liquid composition can be varied.

Thus a further development of the inventive composition provides the fact that the liquid inventive composition comprises a viscosity of between 1 mPas and 100 mPas, preferably between 5 mPas and 25 mPas, before the spraying.

In order to avoid the already afore mentioned problems of solving, dispersing and/or emulsifying the at least one active substance in the inventive liquid composition, in another embodiment of the inventive liquid composition the active substance concentration in the inventive liquid composition is selected in that way that the concentration of the at least one active substance of the preparation formed on the sprayed body surface is between 25% and 500%, preferably between 50% and 150%, higher than the concentration of the active substance of the composition before the spraying.

As already mentioned above in connection with the main claim, a particularly suitable embodiment of the inventive liquid composition comprises only at least one liquid or a liquid mixture additionally to the at least one active substance, so that the preparation formed on the sprayed body surface consists of only at least one active substance after the evaporation or the vaporization of the liquid or the liquid mixture. Hereby this active substance is provided then in a high concentration and in an extremely fine division on the sprayed body surface, whereby the migration and the diffusion of this at least one active substance into the body and/or into the body liquid is accelerated.

Depending on the respective at least one active substance, on the used liquid, respectively on the used liquid mixture, and the possible further ingredients, as for example the later described gel-forming agent, the inventive liquid composition is a dispersion, solution and/or a suspension. Hereby the inventive liquid composition contains as liquid, respectively as liquid mixture, a pharmaceutically harmless organic solvent, respectively a pharmaceutically harmless solvent mixture, and/or water.

The inventive liquid composition preferably contains as organic solvent, respectively as organic solvent mixture, one or several alcohols which can easily be evaporated. The low molecular and easily evaporatable alcohols, as particularly ethanol, propanol-1, propanol-2 and/or butanol, proved to be particularly suitable, whereby preferably ethanol or propanol-2 of a mixture thereof is used. It is also possible to provide in the inventive composition propylenglycol alone or in a mixture with the afore mentioned alcohols as organic solvent. If the inventive liquid composition contains butanol as organic solvent, it is suitable to limit the concentration of this butanol in the inventive composition to an upper limiting value of about 15% by weight relative to the ready-to apply liquid composition, in order to thus maintain the initially indicated formation times of the preparation on the sprayed body surface within a very short time, preferably within less than 4 seconds and particularly within a time of less than 2 seconds and preferably within in a time of between 1 second and 0.01 seconds.

In respect to the total concentration of the alcohol, respectively the alcohol mixture, in the inventive liquid composition it is to be noted that this concentration varies preferably between 5% by weight and 40% by weight and particularly between 7% by weight and 30% by weight. In order to avoid the occurrence of skin irritations for highly sensitive patients caused by alcohols, the percentage by weight of the alcohol, respectively of the alcohol mixture, can be furtherly reduced, so that in this particularly preferred embodiment of the inventive liquid composition the concentration of the alcohol, respectively the alcohol mixture, varies between 13% by weight and 18% by weight relative to the ready-to-apply liquid composition.

The afore mentioned pharmaceutically harmless organic solvents in the inventive liquid composition can certainly also be substituted by water or mixed with water. If the inventive composition does not comprise an alcohol but only water, the risk of the occurrence of skin irritations is hereby totally eliminated for highly sensitive patients, so that in this case the inventive composition comprises additionally to the water only the at least one active substance, as far as the subsequently described ingredients, particularly the gel-forming agents, are not being added to the inventive composition.

If, however, the inventive composition contains a mixture of alcohols and water, the alcohol concentration of the inventive composition varies, under the consideration of the afore indicated explanations, between 5% by weight and 40% by weight and the water concentration varies between 90% by weight and 50% by weight, each relative to the ready-to-apply liquid composition, whereby the percentages by weight missing to sum up the 100% by weight fall to the at least active substance, to a gel-forming agent possibly existing in the inventive composition, the gel-forming agent being subsequently described, and to further ingredients, as particularly preservatives or buffer.

A particularly advantageous development of the inventive liquid composition provides that the liquid composition comprises, if necessary, a preservative or a buffer in addition to the afore indicated components, meaning the at least one active substance, of the liquid, respectively the liquid mixture, and furthermore at least one gel-forming agent. Hereby it was surprisingly observed that the adding of the at least one gel-forming agent supports the formation of nebulous droplets during the spraying of the inventive liquid composition and leads moreover to the fact that, after the spraying, the composition forms a gel-like preparation on the sprayed surface within a very short time, preferably within the afore mentioned times. According to this preferred embodiment of the inventive liquid composition a gel-like preparation is thus formed on the sprayed body surface, whereby this gel-like preparation comprises the at least one active substance, the at least one gel-forming agent as well as certain possible portions of the liquids of existing in the original liquid composition. Hereby the composition and thus the at least one active substance are fixed particularly secure and tight at the correspondingly sprayed body surface, particularly on the sprayed skin of mucous membrane, so that on this body surface a deposit of the at least one active substance is then formed which guarantees that the active substance is constantly added to the body liquid, particularly to the blood, and/or to the locally limited infections and/or to the injuries.

According to the above described development of the inventive liquid composition in which a gel-like preparation is formed after the nebulous spraying on the sprayed body surface, the concentration of the at least one gel-forming agent varies in the composition between 0.5% by weight and 20% by weight, preferably between 2% by weight and 14% by weight, each relative to the ready-to-apply liquid composition before its spraying. In other words, such a liquid composition thus contains between 0.5% by weight and 20% by weight of the at least one gel-forming agent, between 0% by weight and 40% by weight of a pharmaceutically harmless organic solvent or solvent mixture of the afore described sort, the at least one active substance of the afore mentioned sort and the concentration indicated in the patent application, between 0% by weight and 2% by weight of a preservative and/or buffer, and water in a weight amount which together with the afore mentioned components equals the 100% by weight.

In respect to the afore mentioned pharmaceutically harmless organic solvent, respectively the solvent mixture, the same explanations as they are described above are identically valid also for this development of the inventive liquid composition.

The afore described development of the inventive liquid composition may contain as gel-forming agents synthetical gel-forming agent, as for example polymers, particularly polyacrylates, cellulose derivatives, polyvinylalcohols and/or polyvinylacetate.

It is, however, particularly suitable when the inventive liquid composition contains as gel-forming agent a natural gel-forming agent, preferably a phospholipide or a phospholipide mixture and particularly phospholipide, respectively a phospholipide mixture isolated from soybeans, sunflowers and/or eggs. Such phospholipidic gel-forming agents show moreover the advantage that they have, on one hand, a high skin- and tissue-compatibility which supports the penetration of the at least one active substance in the skin and/or through the skin barrier into the body liquid and/or particularly into the blood and that, on the other hand, they effectively protect the at least one active substance against the chemical degradation. Furthermore, it could be surprisingly observed that by applying such phospholipidic gel-forming agents it is made possible to manufacture transparent liquid composition which can be controlled in a correspondingly easy way, so that hereby a plugging of the nozzle of a corresponding spraying device, the nozzle to be used for the spraying inventive liquid composition, is avoided. The phospholipidic gel-forming agents do also not tend to dry out at the spraying nozzle and thus to close the outlet nozzle, which can be referred to the fact that the phospholipidic gel-forming agents being described later in a particularly preferred embodiment have a high durability caused by their hydrophilicity, and that furthermore the phospholipidic gel-forming agents can easily be taken up by the liquid of the inventive liquid composition even when the liquid being bound therein is evaporated, so that during a further spraying the nozzle is correspondingly cleaned from the dried out composition.

In a particularly suitable embodiment of the inventive composition the inventive liquid composition comprises as gel-forming agent a phospholipide, respectively a phospholipide mixture, containing at least 60% by weight phosphatidylcholine, preferably at least 76% by weight phosphatidylcholine, and particularly at least 90% by weight phosphatidylcholine, whereby this concentration indications of the phosphatidylcholine refer to the concentration of the gel-forming agent in the inventive liquid composition.

The afore described positive characteristics of this development of the inventive composition are furtherly improved particularly when in another embodiment of the inventive composition the composition contains as at least one gel-forming agent a phospholipide, respectively a phospholipide mixture, consisting of at least 95% by weight phosphatidylcholine.

In order to reproducibly guarantee the initially described fine division of the at least one active substance in the inventive liquid composition comprising as gel-forming agent the afore mentioned phospholipide with the there indicated high concentration of phosphatidylcholine, a variation of the inventive composition provides that hereby the concentration of lysophosphatidylcholine in the phospholipidic gel-forming agent is limited to a maximum value of 6% by weight, particularly to a maximum value of 4% by weight, relative to the amount of the phospholipidic gel-forming agent in the inventive liquid composition.

Phosphatidylcholine in terms of the present description is in the chemically sense a 1,2-diacylglycero-3-phosphocholine (3sn-phosphatidylcholine), whereby this 1,2-diacylglycero-3-phosphocholine can contain corresponding acylic residues in the 1-position as well as in the 2-position.

A particularly preferred development of the inventive liquid composition comprises as phospholipidic gel-forming agent a phosphatidylcholine which contains acyl residues in the 1- and 2-position that consist between 10 and 15% by weight of the palimitic acid residue, between 1.5 and 4% by weight of the stearic acid residue, between 3 and 10% by weight of the oleic acid residue, between 61 and 71% by weight of the linoleic acid residue and between 3 and 7% by weight of the linolenic acid residue. Hereby the afore mentioned fluctuations of the percentage indications for each acyl residue depend on the fact that the phosphatidylcholine preferably used as gel-forming agent in the inventive composition is such a phosphatidylcholine which is isolated from natural sources, particularly from soybeans, from sunflowers and/or from eggs and which was corresponding cleaned.

Another embodiment of the inventive liquid composition comprises as phospholipidic gel-forming agent a hydrated phospholipide, respectively a hydrated phospholipide mixture, in the concentration generally mentioned above in connection with the gel-forming agent.

In the inventive liquid composition also such a hydrated phospholipide mixture can be used as gel-forming agent that has a phosphatidylcholine content which varies within the limits indicated above for the non-hydrated phospholipide mixture, whereby the phosphatidylcholine of the hydrated phospholipide mixture in the 1- and 2-position then consists as acyl residues 85% by weight ±3% by weight of stearic acid residue and 15% by weight ±2% by weight of palmitic acid residue.

As it is already described above, the inventive liquid composition comprises as gel-forming agent preferably such a phospholipide mixture which contains phosphatidylcholine in the afore mentioned concentrations as main component. In addition to this phosphatidylcholine the phospholipide mixture contains preferably as a maximum 6% by weight lysophosphatidylcholine, 0–12% by phosphatidylethanolamine, 0–8% by weight phosphatidylinositol and/or 0–8% by weight phosphatidic acid, whereby the afore mentioned fluctuations of the concentration indications of the further phospholipidic components can be explained by the fact that the phospholipide mixture used as gel-forming agent was preferably isolated from a natural source. Moreover, the phospholipide mixture can contain low portions of oils and/or stearins, whereby the afore mentioned concentration indications do not refer to the ready-to-apply inventive liquid composition but to the phospholipide mixture itself existing as gel-forming agent.

In respect to the term water used in the present application, it is to be noted that this term water does not only mean water itself, meaning thus distilled water or deionized water, but also all aqueous systems, as particularly salt- or buffer-solutions, preferably phosphate buffers.

A particularly advantageous development of the afore described embodiments of the inventive liquid composition forming a gel-like preparation during a topical application and/or after the spraying onto the body zone, provides the fact that the liquid composition is a dispersion containing liposomes, whereby this preferably clear to slightly opaque liquid composition comprises then as ingredient the at least one active substance, at least one of the afore described phospholipidic gel-forming agents as well as the afore described liquids, respectively liquid mixtures, and, if necessary, furthermore preservatives or buffers in the afore indicated concentration. This development of the inventive liquid composition subsequently forms a vesicular liposomic gel on the sprayed body surface within the afore indicated times, whereby, on one hand, it is avoided that the sprayed liquid dispersion flows off the body surface and, on the other hand, it is guaranteed that not only the at least one active substance is transported in a high concentration and in an extremely fine division through the skin barrier and then reaches the treatment area but that at the same time a deposit of the at least one active substance is formed on the sprayed body surface.

In respect to the concentration of the afore described phospholipidic gel-forming agent, it is to be noted that this concentration, as already explained above, varies between 0.5% by weight and 20% by weight, preferably between 2% by weight and 14% by weight. Particularly good results can be obtained when the phospholipidic gel-forming agent in the inventive liquid composition has a concentration of between 5% by weight and 14% by weight, preferably between 8% by weight and 12% by weight, whereby these concentration indications depend on the viscosity to be adjusted in the liquid composition, on the droplet size to be obtained during the spraying and on the chemical construction of the phospholipidic gel-forming agent. Particularly good results and healing effects can be achieved when the phospholipidic gel-forming agent in the inventive liquid composition has a concentration of about 10% by weight relative to the ready-to-apply liquid composition.

It is furthermore to be noted that the inventive liquid composition, particularly the embodiments of the inventive liquid composition which contain a phospholipidic gel-forming agent, have a pH-value which varies between 5.0 and 8.0 and which lies preferably at about 6.5. Hereby this pH-value can be adjusted by adding a suitable buffer.

In respect to the concentration of the at least one active substance of the inventive composition, it is to be noted that this concentration depends, on one hand, on the respective active substance, meaning on the penetration capacity of the active substance through the skin- or tissue barriers, on the solubility of the active substance and/or on the required treatment concentration at the site of action and, on the other hand, on the infection to be correspondingly treated, on the treatment manner, meaning locally or systemically, and on the frequency of the corresponding daily application. Usually the active substance concentration varies in the inventive composition between 0.01% by weight and 20% by weight, preferably in a concentration of between 0.5% by weight and 10% by weight.

In respect to the active substance existing in the inventive composition, it is generally to be noted that herefore basically each active substance is suitable which is able during a topical application to penetrate the skin barriers or the cell wall barriers and to produce a local effect and/or to be taken up subsequently by a suitable body liquid, preferably blood, in order to be then transported to the respective site of action.

In the following preferred active substances are mentioned which can exist in the inventive composition, whereby the indicated active substances are then selected depending on the respectively desired treatment effect and the corresponding infection without limiting the present invention.

As already initially described in detail in the main claim, the inventive composition can comprises as at least one active substance at least one analgesic and/or anti-rheumatic active substance selected from the group consisting of acemetacine, diclofenac and the salts thereof, preferably diclofenac-sodium and/or dicolfenac-diethylamine, etofenamate, flufenamic acid, ibuprofene, racemic forms and/or enantiomers of ibuprofene, preferably S(+)-ibuprofene, indometacine, ketoprofene, racemic forms and/or enantiomers of ketoprofene, piroxicam, salicylic acid and/or derivatives thereof, preferably acetylsalicylic acid and/or 2-hydroxyethylsalicylic acid. The inventive composition preferably comprises an active substance selected from the group consisting of cylcooxygenase-2 selective non-steroid anti-rheumatics/anti-allergics.

In addition to these active substances or instead of these active substances the inventive composition can comprise as active substance at least one opiate receptor agonist and/or opiate receptor antagonist which is selected from the group consisting of buprenorphine, fentanyl, pentazocine, pethidine, tilidine, tramadol and/or naloxone.

In addition or instead of the afore mentioned active substances the inventive composition can comprise as active substance at least one substance inhibiting the blood coagulation and/or a substance inhibiting the platelet aggregation which is selected form the group consisting of heparin, low molecular heparin, heparin-salts, preferably heparin-sodium and/or heparin-calcium, heparinoids and/or acetylsalicylic acid and/or esters thereof.

It is also possible that the inventive composition comprises as active substance heparin, low molecular heparin, heparin-salts, preferably heparin-sodium and/or heparin-calcium and/or the heparinoids, whereby this active substance, respectively these active substances in the inventive composition preferably have a concentration of between 250,000 I.E. and 2,500,000 I.E. per 100 g of the composition. Hereby the abbreviation I.E. means “Internationale Einheiten” (international units). Such high heparin concentrations can not be applied with usual ointments or creams, so that patients who have to undergo a treatment, for example, after an operation for thrombo-embolism-prophylaxis or for the prophylaxis of thrombo-embolic infections, for the therapy of arterial and/or venous thromboses, of embolisms, of heart attacks and instable angina pectoris, for the coagulation inhibition during the treatment or during the operation with extracorporeal circulation and for the treatment of blood coagulation trouble as a consequence of an increase of thrombocytes as well as of plasmatic coagulation factors, have to be submitted to a several injections during one day when the usual injections are applied.

If, contrarily to that, the heparin, the low molecular heparin the heparin-salts, preferably the heparin-sodium and/or the heparin-calcium, are to be used for the local application to sports injuries and accident injuries, bruises, varicose symptom complexes, superficial thromboses, thrombophlebitides, inflammable infiltrates, cicatricial hardening and/or haemorrhoids, the active substance, respectively the corresponding active substance mixture, has a concentration in the inventive composition of at least 20,000 I.E., preferably however a concentration of between 120,000 I.E. and 240,000 I.E.

It is furthermore possible that the inventive composition comprises at least one corticoid active substance which is selected from the group consisting of dexamethasone, betamethasone, triamcinolone and/or clobetasole.

If the inventive composition comprises as active substance at least one histamine antagonist, this histamine antagonist is selected from the group consisting of bamipine lactate, chlorophenoxamine-HCL, clemastinhydrogenfumaric salt (chemical name: 2-(2-[1-(4-chlorphenyl)-1-phenylethoxy]-ethyl)-1-methylpyrrolidine-hydrogenfumaric salt), dimetidindenmaleate, loratadine and/or pheniraminohydrogenmeleate.

The inventive composition can also comprises as active substance at least one anti-diabetic active substance, preferably an active substance on the basis of insulin.

It is also suitable when the inventive composition comprises as active substance at least one chemotherapeutic, preferably at least one antibiotic, selected from the group consisting of erythromycin, tetracycline HCl, neomycinsulphate, bacitracin, chloroamphenicole; and/or a cytostatic and/or at least a metastasis inhibitor.

In addition to the afore indicated antibiotics, antimycotics and/or in addition to the afore described corticoids, as dermatologically effective substances (dermatics) which can exist as active substances in the inventive composition, specific tretinoin, isoprenalinsulphate, lidocaine HCl, dithranol, urea and/or the known enzyme preparations for the treatment of skin defects can be furthermore mentioned, whereas the local anaesthetics consist preferably of lidocaine-HCl, benzocaine and/or tetracaine.

Moreover, the inventive composition may comprise at least one active substance against influenzal infections and/or colds, preferably an antitussive, an expectorant and/or an secretolytic drug, whereby the alpha-lipoic acid is preferably selected from the neuropathy preparations.

The inventive composition can also contain quinine and/or thalidomide as active substance.

It is furthermore possible that the inventive composition comprises as active substance at least one regulatory peptide and/or the inhibitors thereof which is, respectively are, selected from the group consisting of antuitary hormones and/or the inhibitors thereof, postpituitary hormones and/or the inhibitors thereof, hypothalamic hormones and/or the inhibitors thereof.

If the inventive composition is used for the systemic treatment of viral infections or of virally induced infections, the composition comprises aciclovir as antiviral active substance.

Moreover it is possible that the inventive composition comprises as active substance prostaglandins, preferably $PGE_1$ as well as ester, particularly the ethylester.

The afore mentioned heparin is either a standard heparin with a molecular weight of between about 3,000 and 30,000, preferably with an average molecular weight of between 12,000 and 15,000, and/or a low molecular heparin with a average molecular weight of about 4,000 to 6,000.

If the inventive liquid composition is a liposome dispersion or if the composition contains liposomes, it comprises particularly vesicles with an average diameter of between 70 nm and 500 nm, preferably with an average diameter of between 80 nm and 120 nm, whereby these vesicles have particularly one to three skins (membranes).

For the manufacturing of the afore described liquid composition comprising a phospholipidic gel-forming agent, firstly the phospholipides are swollen and pre-hydrated in a part of the water, so that the lamellar phase can form in the aqueous surrounding. Subsequently the at least one active substance is taken up from the water and added. The thus obtained mixture is homogenized by being submitted to high energy, particularly by means of a high pressure homogenizer or of a splitting homogenizer. After being thoroughly homogenized, the possibly missing amount of water, of the buffer and/or the pharmaceutically harmless organic solvent, respectively the solvent mixture, are added. If the desired liposomes being quantified above by their diameter are to be generated, it is suitable to manufacture this desired liposome size by varying the time of homogenization and by correspondingly applying energy.

As already repeatedly described, the inventive liquid composition is sprayed under the formation of nebulous droplets. Herefore particularly a spraying device is used which preferably operates without a blowing agent and which comprises a pump sprayer, whereby 20 to 300 $\mu$l of the liquid composition per spraying, particularly with a droplet size of between 1 $\mu$m and 1,000 $\mu$m, preferably with a droplet size of between 10 $\mu$m and 100 $\mu$m, are emitted by means of a suitable spraying nozzle.

A particularly preferred and special embodiment of the afore described inventive liquid composition being applicable to sports injuries and accident injuries, bruises, varicose symptom complexes, superficial thromboses, thrombophlebitides, inflammable infiltrates, cicatricial hardening and/or haemorrhoids, is a liposomal dispersion and comprises, relative to the ready-to-apply composition, about 10% by weight of a phospholipidic gel-forming agent of the afore indicated sort, whereby this phospholipidic gel-forming agent contains particularly between 73% by weight and 80% by weight of phosphatidylcholine relative to the total amount of the gel-forming agent. Furthermore, the embodiment optionally comprises 120,000 I.E. or 240,000 I.E. of heparin per 100 g of the liquid composition, whereby this liquid composition contains about 16% by weight ethanol. The remaining portion of the composition is water, whereas the pH-value of this special embodiment of the liquid composition lies at about 6.5. This pH-value is adjusted by means of a suitable phosphate buffer ($KH_2PO_4$/$Na_2HPO_4$).

Advantageous developments of the inventive liquid composition are indicated in the subclaims.

The inventive liquid composition is subsequently described in detail by means of examples.

The phospholipidic gel-forming agent used in the examples 1 to 6 had the following composition:

76±3% by weight of phosphatidylcholine,

0–6% by weight of lysophosphatidylcholine,

0–8% by weight of phosphatidic acid,

0–4% by weight of phosphatidylethanolamine and about 9% by weight of other usual accompanying lipides not being analysed in detail.

The phosphatidylcholine in the phospholipidic gel-forming agent contained in its 1- and 2-position the acyl residues:

10–15% by weight of palmitic acid residue, 1.5–4% by weight of stearic acid residue, 6–13% by weight of oleic acid residue, 61–71% by weight of linoleic acid residue and 4–7% by weight of linolenic acid residue.

EXAMPLE 1

The pharmaceutical composition manufactured according to example 1 had the following ingredients:

10 g phospholipidic gel-forming agent, 16 g ethanol, 1 g acemetacine, 0.5 g phosphate buffer (solid) and distilled water (about 72.5 g) ad 100 g of the pharmaceutical composition.

In order to manufacture the afore mentioned pharmaceutical composition according to the example, the 10 g of the phospholipidic gel-forming agent were swollen in about 30% by volume of the total amount of the water. The active substance acemetacine being solved in ethanol was then added to this swollen phospholipidic gel-forming agent. Subsequently the thus obtained mixture was submitted to a high pressure homogenizer, whereby the remaining water amount as well as the buffer were added. During this homogenization the vesicle size was constantly controlled, whereby, after obtaining an average particle size of a diameter of about 100 nm, the homogenization was interrupted. The pH-value of the transparent slightly opaque dispersion was 6.5.

EXAMPLE 2

As described in example 1 a second embodiment of the pharmaceutical composition was manufactured, whereby this second embodiment differs from the firstly described embodiment in that way that the amount of the phospholipidic gel-forming agent was reduced from 10 g to 7 g and that the 1 g of the acemetacine was replaced by 2 g of S(+)-ibuprofene.

The pH-value of the dispersion was 7 (adjusted with caustic soda). The manufacturing procedure of the pharmaceutical composition according to example 2 was conform to the manufacturing procedure according to example 1.

EXAMPLE 3

A pharmaceutical composition comprising 2 g diclofenac-sodium, 5 g phospholipidic gel-forming agent, 15 g propanol-2, 7 g propylenglycol, hydrochloric acid to adjust a pH-value of 6.9 and water ad 100 g of the composition was manufactured, as this is described above. Hereby the clear and transparent dispersion had a particle size of about 80 nm (particle diameter).

EXAMPLE 4

The pharmaceutical composition manufactured according to example 4 comprised the following ingredients:

2.5 g phospholipidic gel-forming agent, 16 g ethanol, 1,600,000 I.E. heparin-sodium (content: at least 150 I.E/mg), 0.5 g phosphate buffer (solid) and distilled water (about 66 g) ad 100 g of the pharmaceutical composition.

In order to manufacture the afore mentioned pharmaceutical composition accordingly to example 4, the 2.5 g of the phospholipidic gel-forming agent were swollen in the about 1/10 of the total water amount. The heparin-sodium solved almost in the total amount of the remaining water was then added to this swollen phospholipidic gel-forming agent. Subsequently, the thus manufactured mixture was submitted to a high pressure homogenizer. During this homogenization the vesicle size was constantly controlled, whereby, after obtaining an average particle size of a diameter of about 75 nm, the afore indicated amount of ethanol was added. Hereafter the pH-value of the phosphate buffer was adjusted to 6.5.

EXAMPLE 5

The pharmaceutical composition manufactured according to example 5 comprised the following ingredients:

10 g phospholipidic gel-forming agent, 16 g ethanol, 120,000 I.E. heparin-sodium (content: at least 120 I.E./mg), 0.5 g phosphate buffer (solid) and distilled water (about 72.5 g) ad 100 g of the pharmaceutical composition.

In order to manufacture the afore mentioned pharmaceutical composition accordingly to example 5, the 10 g of the phospholipidic gel-forming agent were swollen in the about 1/10 of the total water amount. The heparin-sodium solved almost in the total amount of the remaining water was then added to this swollen phospholipidic gel-forming agent. Subsequently, the thus manufactured mixture was submitted to a high pressure homogenizer. During this homogenization the vesicle size was constantly controlled, whereby, after obtaining an average particle size of a diameter of about 75 nm, the afore indicated amount of ethanol was added. Hereafter the pH-value of the phosphate buffer was adjusted to 6.5.

EXAMPLE 6

As described in example 5 a sixth embodiment of the pharmaceutical composition was manufactured, whereby this sixth embodiment differed from the afore described fifth embodiment in that way that the concentration of the heparin-sodium-active substance was 240,000 I.E. lag. Correspondingly to that the sixth embodiment comprised a slightly smaller water amount.

Whereas the afore described pharmaceutical composition are mainly systemically applied accordingly to the examples 1 to 4, the examples 5 and 6 described such pharmaceutical compositions which are applied to local injuries, particularly to sports injuries and accident injuries, bruises, varicose symptom complexes, superficial thromboses, thrombophlebitides, inflammable infiltrates, cicatricial hardening and/or haemorrhoids.

All six embodiments of the liposomal dispersions manufactured according to examples 1 to 6 are clear to slightly opaque dispersions which are sprayed from a usually formed pump sprayer under the formation of nebulous droplets. Per spraying the pump sprayer emitted about 200 μl of the dispersion.

A vertically fixed glass plate was sprayed from a distance of 30 cm with the afore mentioned usual pump sprayer, whereby a sieve with a mesh-size of 200 was arranged exactly in the middle between the glass plate and the pump sprayer, meaning thus 15 cm of distance to the pump sprayer.

Firstly the pump sprayer was filled with distilled water. During the spraying of the glass plate it was, however, observed that the spraying did not penetrate the afore indicated sieve and that thus the water flew down the vertically fixed sieve surface.

Hereafter the pump sprayer was filled with a solution of heparin-sodium (800,000 I.E. per 100 g of the composition) and the afore mentioned spraying test was repeated several times. Hereby it was observed that about 50% by volume of the sprayed amount per spraying penetrated the sieve surface, reached the glass plate and there dried out so fast that a thin relatively regular layer of the heparin-sodium was formed on the glass plate.

The pump sprayer was filled with the composition described in example 1. Hereafter the afore described glass plate was repeatedly sprayed, whereby accordingly to example 1 only about 10% by volume of the sprayed composition was retained from the sieve surface. 90% by volume spontaneously formed a gel on the glass surface, whereby this gel did not flow down the glass surface.

The pump sprayer was filled with the composition described in example 2. During the spray test it was observed that only about 15% by volume of the sprayed amount per spraying did not penetrate the sieve surface, whereas 85% by volume of the sprayed amount reached the glass plate and spontaneously formed a gel thereon which did not flow down the glass plate.

The pump sprayer was filled with the composition described in example 3. During the spray test it was observed that only about 8% by volume of the sprayed amount per spraying did not penetrate the sieve surface, whereas 92% by volume of the sprayed amount reached the glass plate and spontaneously formed a gel thereon which did not flow down the glass plate.

The pump sprayer was filled with the composition described in example 4. During the spray test it was observed that only about 6% by volume of the sprayed amount per spraying did not penetrate the sieve surface, whereas 94% by volume of the sprayed amount reached the glass plate and spontaneously formed a gel thereon which did not flow down the glass plate.

The pump sprayer was filled with the composition described in example 5. During the spray test it was observed that only about 10% by volume of the sprayed amount per spraying did not penetrate the sieve surface, whereas 90% by volume of the sprayed amount reached the glass plate and spontaneously formed a gel thereon which did not flow down the glass plate.

The pump sprayer was filled with the composition described in example 6. During the spray test it was observed that only about 5% by volume of the sprayed amount per spraying did not penetrate the sieve surface, whereas 95% by volume of the sprayed amount reached the glass plate and spontaneously formed a gel thereon which did not flow down the glass plate.

The afore mentioned results show that only the water sprayed by means of the used pump sprayer produced droplets during the spraying with a droplet diameter of over 74 μm. The aqueous heparin solution as well as the composition manufactured according to the examples 1 to 6 comprised droplets with a diameter of less than 74 μm.

In a test with ten female test persons, each of them suffering from a chronical phlebitis, the composition described in example 5 was tested. Hereby the composition was filled according to example 5 into the afore mentioned pump sprayer, whereby the test persons were asked to apply three times per day correspondingly three sprayings, so that in total about 1.800 $\mu$l of the composition were applied each day.

Before this all test persons had treated their phlebitis with the usual heparin-containing ointment having a heparin-content of 120,000 I.E.

Already at the beginning of the test eight test person reported in accordance but independently from each other that they experience the application of the spray dispersion as essentially more pleasant and as taking less time than the usually used heparin-containing ointment. The test persons particularly observed that no undesired smearing and soling of the cloths occurred, so that the spray dispersion was also applied during the working hours. Moreover, all test persons reported in accordance that after spraying the composition according to example 5 a cooling and a spontaneous pain relieve was noted, which was not the case concerning the application of the usual ointment. Six test persons who had used the heparin-containing ointment before the application of the spray dispersion over a time period of four weeks and who observed only an insignificant healing process, were healed within twelve days after having begun to apply the spray dispersion according to example 5.

We claim:

1. A pharmaceutical composition containing at least one systemically and/or locally effective, topically applicable active substance, wherein the composition has such a liquid consistency that it is sprayable as liquid droplets, and that after being sprayed the composition forms a preparation within a time of less than 4 seconds, on the sprayed body surface, particularly on the sprayed skin or mucous membrane, which contains the active substance in a finely divided way and in which the concentration of said at least one active substance is between 25% and 500% higher than the concentration of said at least one active substance in said liquid composition before the spraying.

2. The pharmaceutical composition according to claim 1 wherein the composition forms the preparation on the sprayed body surface within a time of less than 2 seconds.

3. The pharmaceutical composition according to claim 1, wherein the composition is sprayable as a droplet with a droplet diameter of between 1 $\mu$m and 1,000 $\mu$m.

4. The pharmaceutical composition according to claim 1 wherein before being sprayed the composition has a viscosity of between 1 mPas and 100 mPas.

5. The pharmaceutical composition according to claim 1 wherein the concentration of the at least one active substance of the preparation formed on the sprayed body surface is between 50% and 150%, higher than the concentration of the at least one active substance of the composition before the spraying.

6. The pharmaceutical composition according to claim 1 wherein the composition comprises only at least one liquid or a liquid mixture additionally to the at least one active substance, so that the preparation formed on the sprayed body surface consists of at least one active substance.

7. The pharmaceutical composition according to claim 1 wherein the liquid composition is a dispersion, solution and/or a suspension and that the composition contains as liquid, respectively as liquid mixture, a pharmaceutically harmless organic solvent, respectively a solvent mixture, and/or water.

8. The pharmaceutical composition according to claim 6, wherein the organic solvent comprises an alcohol or an alcohol mixture which are easily vaporizable.

9. The pharmaceutical composition according to claim 6, wherein the concentration of the alcohol, respectively the alcohol mixture, in the liquid composition varies between 5% by weight and 40% by weight relative to the liquid composition.

10. The pharmaceutical composition according to claim 6, wherein the liquid composition contains between 90% by weight and 50% by weight water.

11. The pharmaceutical composition according to claim 1, wherein the liquid composition furthermore contains at least one gel-forming agent in such as way that, after being sprayed, the composition forms a gel-like preparation on the sprayed body surface within a very short time.

12. The pharmaceutical composition according to claim 11, wherein the concentration of the gel-forming agent in the composition varies between 0.5% by weight and 20% by weight, relative to the liquid composition.

13. The pharmaceutical composition according to claim 11, wherein the composition comprises as gel-forming agent a phospholipid or a phospholipid mixture.

14. The pharmaceutical composition according to claim 13, wherein the composition comprises as gel-forming agent a phospholipid, respectively a phospholipid mixture, which contains at least 60% by weight phosphatidylcholine.

15. The pharmaceutical composition according to claim 13, wherein the composition comprises as gel-forming agent a phospholipid, respectively a phospholipid mixture, which contains at least 95% by weight phosphatidylcholine.

16. The pharmaceutical composition according to claim 13, wherein the phospholipid mixture comprises as a maximum 6% by weight lysophosphatidylcholine.

17. The pharmaceutical composition according to claim 13, wherein the composition comprises a phosphatidylcholine which contains acyl residues in the 1- and 2-position that consist between 10 and 15% by weight of the palimitic acid residue, between 1.5 and 4% by weight of the stearic acid residue, between 3 and 10% by weight of the oleic acid residue, between 61 and 71% by weight of the linoleic acid residue and between 3 and 7% by weight of the linolenic acid residue.

18. The pharmaceutical composition according to claim 13, wherein the composition comprises as gel-forming agent a hydrated phospholipid, respectively phospholipide mixture.

19. The pharmaceutical composition according to claim 18, wherein the phosphatidylcholine existing in the hydrated phospholipid, respectively phospholipid mixture, consists in the 1- and 2-position 85% by weight ±3% by weight of the stearic acid residue and 15% by weight ±2% by weight of the palmitic acid residue.

20. The pharmaceutical composition according to claim 13, wherein, additionally to the phosphatidylcholine as main component and the at maximum 6% by weight lysophosphatidylcholine, the phospholipid mixture comprises furthermore 0–12% by weight phosphatidylethanolamine, 0–8% by weight phosphatidylinositol and/or 0–8% by weight phosphatidic acid.

21. The pharmaceutical composition according to claim 13, wherein the liquid composition is a dispersion and contains liposomes.

22. The pharmaceutical composition according to claim 1 wherein the composition comprises the active substance in a concentration of between 0.01% by weight and 20% by weight.

23. The pharmaceutical composition according to claim 1, wherein the composition comprises at least one analgesic and/or anti-rheumatic active substance which is selected from the group consisting of acemetacine, diclofenac and the salts thereof, preferably diclofenac-sodium and/or dicolfenac-diethylamine, exofenamate, flufenamic acid, ibuprofene, racemic forms and/or enantiomers of ibuprofene, preferably S(+)-ibuprofene, indometacine, ketoprofene, racemic forms and/or enantiomers of ketoprofene, piroxicam, salicylic acid and/or derivatives thereof, preferably acetylsalicylic acid and/or 2-hydroxyethylsalicylic acid, and/or from the cylcooxygenase-2 selective non-steroid anti-rheumatics/anti-allergics.

24. The pharmaceutical composition according to claim 1 wherein the composition comprises as active substance at least one opiate receptor agonist and/or opiate receptor antagonist which is selected from the group consisting of buprenorphine, fentanyl, pentazocine, tilidine, tramadol and/or naloxone.

25. The pharmaceutical composition according to claim 1, wherein the composition comprises as active substance at least one substance inhibiting the blood coagulation and/or a substance inhibiting the platelet aggregation which is selected form the group consisting of heparin, low molecular heparin, heparin-salts, preferably heparin-sodium and/or heparin-calcium, heparinoids and/or acetylsalicylic acid and/or esters thereof.

26. The pharmaceutical composition according to claim 25, wherein the composition comprises the heparin, low molecular heparin, heparin-salts and/or the heparinoids in a concentration of between 250,000 I.E. and 2,500,000 I.E. per 100 g of the composition.

27. The pharmaceutical composition according to claim 1, wherein the composition contains the heparin, the low molecular heparin, the heparin-salts and/or the heparinoids in a concentration of at least 20,000 I.E. for the application for sports injuries and accident injuries, bruises, varicose symptom complexes, superficial thromboses, thrombophlebitides, inflammable infiltrates, cicatricial hardening and/or haemorrhoids.

28. The pharmaceutical composition according to claim 27, wherein the composition contains the heparin, the low molecular heparin, the heparin-salts, and/or the heparinoids in a concentration of between 120,000 I.E. and 240,000 I.E.

29. The pharmaceutical composition according to claim 1, wherein the composition comprises at least one corticoid active substance which is selected from the group consisting of dexamethasone, betamethasone, triamcinolone and/or clobetasole.

30. The pharaceutical composition according to claim 1, wherein the composition comprises as active substance at least one histamine antagonist which is selected from the group consisting of bamipine lactate, chlorophenoxamine-HCl, clemastinhydrogenfumaric salt (chemical name: 2-(2-[1-(4-chlorphenyl)-1-phenylethoxy]-ethyl)-1-methylpyrrolidine-hydrogenfumaric salt), dimetidindenmaleate, loratadine and/or pheniraminohydrogenmeleate.

31. The pharmaceutical composition according to claim 1, wherein the composition contains as active substance at least one anti-diabetic active substance.

32. The pharmaceutical composition according claim 1, wherein the composition contains as active substance at least one dermatologically effective substance.

33. The pharmaceutical composition according to claim 1 wherein the composition contains at least one local anaesthetic.

34. The pharmaceutical composition according to claim 1, wherein the inventive composition contains quinine and/or thalidomide as active substance.

35. The pharmaceutical composition according to claim 1, wherein the composition contains as active substance at least one chemotherapeutic.

36. The pharmaceutical composition according to claim 1, wherein the composition comprises as active substance at least one regulatory peptide and/or the inhibitors thereof which is, respectively are, selected from the group consisting of antuitary hormones and/or the inhibitors thereof, postpituitary hormones and/or the inhibitors thereof, hypothalamic hormones and/or the inhibitors thereof.

37. The pharmaceutical composition according to claim 1, wherein the composition comprises aciclovir as antiviral active substance.

38. The pharmaceutical composition according to claim 1, wherein the composition comprises as active substance prostaglandins.

39. The pharmaceutical composition according to claim 1, wherein the active substance is selected from the group consisting of local anaesthetics, anti-allergic agents, dermatics, active substances for infuenzal infections and colds, active substances for the treatment of neuropathies, chemotherapeutics, quinine, thalidomide, analgesics, non-steroid antirheumatics, opiate receptor agonists, opiate receptor antagonists, substances inhibiting blood coagulation, substances inhibiting platelet aggregation, corticoids, histamine antagonists, anti-diabetics, regulatory peptides and the inhibitors thereof, prostaglandins and the esters thereof, and antivirally effective substances.

40. The pharmaceutical composition according to claim 2, wherein the composition forms the preparation on the sprayed body surface within a time of between 0.01 second and 1 second.

41. The pharmaceutical composition according to claim 3, wherein the droplet diameter is between 10 $\mu$m and 100 $\mu$m.

42. The pharmaceutical composition according to claim 4, wherein the viscosity of the composition before being sprayed is between 5 mPas and 25 mPas.

43. The pharmaceutical composition according to claim 11, wherein the concentration of the gel-forming agent in the composition varies between 2% by weight and 14% by weight, relative to the liquid composition.

44. The pharmaceutical composition according to claim 13, wherein the phospholipid or the phospholipid mixture is isolated from soybeans, sunflowers and/or egg.

45. The pharmaceutical composition according to claim 13, wherein the composition comprises as gel-forming agent a phospholipid, respectively a phospholipid mixture, which contains at least 76% by weight phosphatidylcholine.

46. The pharmaceutical composition according to claim 13, wherein the composition comprises as gel-forming agent a phospholipid, respectively a phospholipid mixture, which contains at least 90% by weight phosphatidylcholine.

47. The pharmaceutical composition according to claim 13, wherein the phospholipid mixture comprises as a maximum 4% by weight of lysophosphatidylcholine.

48. The pharmaceutical composition according to claim 1, wherein the composition comprises the active substance in a concentration of between 0.5% by weight and 10% by weight.

49. The pharmaceutical composition according to claim 26, wherein the heparin salts are selected from the group consisting of heparin-sodium and heparin-calcium.

50. The pharmaceutical composition according to claim 31, wherein the at least one anti-diabetic active substance is insulin.

51. The pharmaceutical composition according to claim 33, wherein the at least one local anaesthetic is selected from the group consisting of lidocaine-HCl, benzocaine and tetracaine.

52. The pharmaceutical composition according to claim 35, wherein the at least one chemotherapeutic is an antibiotic, a cytostatic and/or at least one metastasis inhibitor.

53. The pharmaceutical composition according to claim 38, wherein the prostaglandins include $PGE_1$ as well as esters thereof.

54. The pharmaceutical composition according to claim 53, wherein the esters include an ethylester.

* * * * *